United States Patent [19]

Lauterbach et al.

[11] Patent Number: 5,075,489

[45] Date of Patent: Dec. 24, 1991

[54] BETA, GAMMA-UNSATURATED NITRILES, THEIR PREPARATION AND THEIR USE AS SCENTS

[75] Inventors: Gerald Lauterbach, Bensheim; Rainer Becker, Duerkheim; Klaas Jansen, Ludwigshafen, all of Fed. Rep. of Germany

[73] Assignee: BASF Aktiengesellschaft, Ludwigshafen, Fed. Rep. of Germany

[21] Appl. No.: 514,244

[22] Filed: Apr. 25, 1990

[30] Foreign Application Priority Data

Apr. 29, 1989 [DE] Fed. Rep. of Germany ....... 3914391

[51] Int. Cl.$^5$ .................. A61K 7/46; C07C 255/07
[52] U.S. Cl. .......................... 558/462; 512/6; 549/442; 558/388; 558/410
[58] Field of Search .............. 512/6; 558/462, 410, 558/388

[56] References Cited

U.S. PATENT DOCUMENTS

| | | | |
|---|---|---|---|
| 3,531,510 | 9/1970 | Blumenthal | 512/6 X |
| 3,553,110 | 1/1971 | Mitchell et al. | 512/6 X |
| 3,960,923 | 6/1976 | DeSimone | 512/6 X |
| 4,028,395 | 6/1977 | Prevedello et al. | 512/6 X |
| 4,132,677 | 1/1979 | Shaffer et al. | 512/6 |
| 4,193,934 | 3/1980 | Bauer et al. | 512/6 X |
| 4,277,377 | 7/1981 | Webb et al. | 512/6 |
| 4,456,561 | 6/1984 | Lenselink | 512/6 X |
| 4,579,680 | 4/1986 | Sell | 512/6 |
| 4,722,808 | 2/1988 | Kaufhold et al. | 512/6 |
| 4,863,631 | 9/1989 | Sprecker et al. | 512/6 X |

FOREIGN PATENT DOCUMENTS

| | | | |
|---|---|---|---|
| 3400689A1 | 7/1975 | Fed. Rep. of Germany | 512/6 |
| 7713925 | 6/1979 | Netherlands | 512/6 |

OTHER PUBLICATIONS

Organikum, VEB Deutscher Verlag der Wissenschaften, Berlin, 1986, pp. 458–461.
Organikum, VEB Deustscher Verlag der Wissenschaften, Berlin, 1986, pp. 210–213.
Angew. Chem., 86, 1974, Nr. 5, pp. 187–197, E. V. Dehmlow.

*Primary Examiner*—Joseph Paul Brust
*Attorney, Agent, or Firm*—Oblon, Spivak, McClelland, Maier & Neustadt

[57] ABSTRACT

Unsaturated nitriles of the general formula I

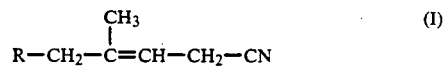

where R is a branched or straight-chain alkyl radical of 4 to 10 carbon atoms or a phenyl ring which is substituted by alkyl of 1 to 4 carbon atoms, one or more alkoxy groups of 1 to 3 carbon atoms, preferably 1 or 2 methoxy groups, or alkylenedioxy, preferably methylenedioxy, and their preparation and their use as scents.

5 Claims, No Drawings

BETA, GAMMA-UNSATURATED NITRILES, THEIR PREPARATION AND THEIR USE AS SCENTS

The present invention relates to unsaturated nitriles of the general formula I $$R-CH_2-\underset{\underset{CH_3}{|}}{C}=CH-CH_2-CN \quad (I)$$

where R is a branched or straight-chain alkyl radical of 4 to 10 carbon atoms or a phenyl ring which is substituted by alkyl of 1 to 4 carbon atoms, one or more alkoxy groups of 1 to 3 carbon atoms, preferably methoxy, or alkylenedioxy, preferably methylenedioxy, and their preparation and their use for imparting fragrance properties to perfumes or to products to be perfumed, or for improving or modifying the fragrance properties of perfumes or of said products Because of the generally poor availability of many natural scent components, the necessity of adaptation to changing fashion trends and the constantly increasing demand for odor improvers for products in daily use, such as cleaners, cosmetics, glues, etc., the scent industry constantly requires new scents which, alone or in the form of compositions, are useful perfumes or fragrance materials having interesting fragrance notes. Since a controlled synthesis of scents having desirable olfactory properties is not possible owing to the fact that little is known about the relationships between structure and scent properties, it is the object to find compounds which have useful scent qualities.

It is an object of the present invention to provide novel and interesting scents which can be prepared in a very simple manner from readily available and therefore cheap starting materials and which furthermore have good stability in a very wide range of media.

We have found that this object is achieved to a surprisingly great extent by the novel unsaturated nitriles of the formula I.

Of particular importance are unsaturated nitriles of the general formula I, where R is $-(CH_2)_n-CH_3$ and n is an integer of from 5 to 8, and nitriles of the general formula I, where R is an aromatic radical of the formula

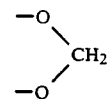

in which Y is H if Z is $-CH_3$;

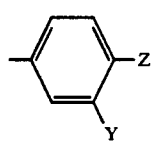

or Y and Z are each $-O-CH_3$ or Y and Z together form the radical

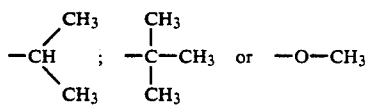

Particular examples are 4,7,9,9-tetramethyldec-3-enenitrile, 4-methyltridec-3-enenitrile, 4-methyldodec-3-enenitrile, 5-(4-methylphenyl)-4-methylpent-3-enenitrile and 5-(4-tert-butylphenyl)-4-methylpent-3-enenitrile.

The nitriles of the formula I can be prepared in a simple manner by subjecting the generally readily and economically available aldehydes of the general formula II $$R-CH_2-\underset{\underset{CH_3}{|}}{CH}-CHO \quad (II)$$

where R has the abovementioned meanings, to a Knoevenagel reaction with cyanoacetic acid.

For this purpose, the aldehyde of the formula II is heated in an inert, water-immiscible solvent, such as benzene, toluene or xylene, or in a basic solvent, such as dimethylformamide or piperidine (Knoevenagel-Doebner reaction) or in a mixture of such solvents and in the presence or absence of ammonium acetate or glacial acetic acid, with separation of water until water separation is no longer observed The reaction mixture is worked up in general by distillation when inert solvents are used or, in the presence of basic solvents, often by pouring the reaction mixture onto ice and then carrying out extraction. Further details on the procedure for such Knoevenagel reactions are given in, for example, Organikum, VEB Deutscher Verlag der Wissenschaften, Berlin, 1986, page 458–461.

Where the allyl halides of the general formula III $$R-CH_2-\underset{\underset{CH_3}{|}}{C}=CH-CH_2-X \quad (III)$$

where R has the abovementioned meansings and X is Cl, Br or I, are readily available, it is advantageous to prepare the nitriles of the formula I by reacting the allyl halides of the general formula III with cyanide ions (cf. Organikum, VEB Deutscher Verlag der Wissenschaften, Berlin, 1986, pages 210–213). In some cases, it is advantageous to carry out the reaction of the allyl halides of the formula III with cyanide ions under phase-transfer catalysis.

For further details of reactions under phase-transfer catalysis, reference may be made to, for example, Dehmlow, Angew. Chem. 86 (1974), 187–197.

The present invention relates not only to β, γ-unsaturated nitriles of the general formula I and their preparation by subjecting the aldehyde of the general formula II to a Knoevenagel reaction with cyanoacetic acid or by reacting the allyl halides of the general formula III with cyanide ions, but also to the use of the nitriles of the formula I for imparting fragrance properties to perfumes or to products to be perfumed, or for improving or modifying the fragrance properties of perfumes or of said products.

Since the odor properties of the nitriles depend to a great extent on the radical R, a wide range of novel scents can be prepared in a simple and economical manner by this process by varying this radical, particularly since the corresponding aldehydes of the formula II are as a rule readily and economically available. In addition to their interesting odor properties and their simple synthesis, the novel nitriles also have surprisingly high stability in neutral as well as weakly acidic and basic media, so that they are suitable for an extremely wide range of uses.

The Example which follow describe the preparation of many unsaturated nitriles of the formula I. In addition to the physical data, the particular fragrance notes of the novel compounds are also stated here.

EXAMPLES 1 TO 8

2 moles of the aldehyde shown in Table 1 were heated with 180 g (2.2 moles) of cyanoacetic acid, 600 ml of toluene and 23.4 g of ammonium acetate while stirring for 3 hours (h) with constant separation of water. The reaction mixture was then cooled and was washed with 500 ml of water. After the aqueous phase had been separated off, the organic phase was distilled under greatly reduced pressure. The names, yields, boiling points and fragrance notes of the resulting unsaturated nitriles are stated in Table 1 below.

3-enenitrile (Example 1) in a composition by way of example. Because of the pronounced odor intensity and the excellent persistence of this compound, even small added amounts had convincing effects in compositions.

| | |
|---|---|
| Dihydromyrcenol | 0.30 g |
| Lysmeral ® (BASF) | 1.40 g |
| p-Tert-butylcyclohexyl acetate | 1.80 g |
| Phenylethyl methyl ether | 0.30 g |
| Jasmorange ® BASF) | 0.50 g |
| Galaxolid ® 50 (IFF) | 0.70 g |
| Cedryl acetate | 0.40 g |
| Styrollyl acetate | 0.10 g |
| Lavandin abrialis | 0.50 g |
| Tetrahydrolinalool | 1.30 g |
| Terpinyl acetate | 1.10 g |
| $C_9$-alcohol | 0.30 g |
| Cyclohexylethanol | 0.10 g |
| Dihdyrorose oxide | 0.30 g |
| Terpineol | 0.20 g |
| Phenylacetic acid, 10% in DPG* | 0.10 g |
| Dimethylheptanol | 0.10 g |
| Citronellol | 0.30 g |
| 4-Methyltridec-3-enenitrile | 0.20 g |
| | 10.00 g |

*DPG = Dipropylene glycol

TABLE 1

| Example | Aldehyde | Nitrile obtained | Yield [g (% of theory)] | bp. [°C./mbar] | Fragrance note |
|---|---|---|---|---|---|
| 1 | 2-Methylundecanal | 4-Methyltridec-3-ene-nitrile | 320 (77%) | 127–130/0.5 | Aldehyde-like, fresh (intense) |
| 2 | 2-Methyldecanal | 4-Methyldodec-3-ene-nitrile | 290 (75%) | 107–113/0.5 | Fresh, citrus, floral (intense) |
| 3 | 3-(4-Methylphenyl)-2-methylpropanal | 5-(4-Methylphenyl)-4-methylpent-3-ene-nitrile | 270 (73%) | 129–136/0.5 | Jasmine, citrus, floral |
| 4 | 3-(4-Isopropylphenyl)-2-methylpropanal | 5-(4-Isopropylphenyl)-4-methylpent-3-ene-nitrile | 260 (61%) | 129–132/0.4 | Aldehyde-like, waxy |
| 5 | 3-(4-Tert-butylphenyl)-2-methylpropanal | 5-(4-Tert-butylphenyl)-4-methylpent-3-enenitrile | 350 (77%) | 139–142/0.3 | Floral |
| 6 | 3-(4-Methoxyphenyl)-2-methylpropanal | 5-(4-Methoxyphenyl)-4-methylpent-3-ene-nitrile | 250 (61%) | 136–140/0.5 | Sweet, herbaceous |
| 7 | 3-(3,4-Dioxymethylenephenyl)-2-methylpropanol | 5-(3,4-Dioxymethylenephenyl)-4-methylpent-3-enenitrile | 268 (58%) | 150–155/0.5 | Floral, green |
| 8 | 3-(3,4-Dimethoxyphenyl)-2-methylpropanol | 5-(3,4-Dimethoxyphenyl)-4-methylpent-3-enenitrile | 268 (58%) | 150–155/0.35 | Sweet |

EXAMPLE 9

Synthesis of 4,7,9,9-tetramethyldec-3-enenitrile 438 g (2.38 moles) of 2,5,7,7-tetramethyloctanal, 202 g (2.38 moles) of cyanoacetic acid, 350 ml of toluene, 350 ml of dimethylformamide and 28.5 g of ammonium acetate were heated under a water separator for 4 h, while stirring. Thereafter, the toluene was distilled off and the remaining residue was heated for 2 h at 180° C. The cooled residue was poured onto ice water and extracted with diethyl ether. The organic phase was washed in succession with NaHCO: solution and water and then distilled. 450 g (yield: 91% of theory) of 4,7,9,9-tetramethyldec-3-enenitrile of boiling point 83°–88° C./-.3 mbar were obtained. The fragrance note was waxy, floral and fresh.

EXAMPLE 10 (Use Example)

The wide range of potential uses of the novel nitriles will be demonstrated using the effect of 4-methyltridec- The novel 4-methyltridec-3-enenitrile imparted a very interesting, fresh, floral note with an ozone-like secondary note to the composition.

EXAMPLE 11

To demonstrate the versatility and the better stability compared with a conventional scent having a very similar fragrance note, a stability comparison, conventional in the scent industry, was made between the novel 4-methtridec-3-enenitrile and the commercial scent methylnonylacetaldehyde ($C_{12}$MNA). For this purpose, samples of the scents were incorporated in various conventional commercial products and in aqueous solutions having different pH values, and the fragrance notes of the test products were tested at room temperature and at 35° C. over a period of 4 months. As shown in the Table below, the stability of the novel compound is superior to that of the known scent in many applications. In the Table below:

| Test medium | 4-Methyltridec-3-enenitrile | C$_{12}$-MNA |
| --- | --- | --- |
| Soap | + | + |
| Washing powder (perborate) | + | + |
| Washing powder (TAED) | ± | − |
| Softener (stability) | ± | + |
| Softener (adhesion to textiles) | + | ± |
| Shampoo | + | ± |
| Bleaching liquor | + | ± |
| Coldwave preparation | + | ± |
| Antiperspirant | + | + |
| pH 1 | − | − |
| pH 2 | − | ± |
| pH 3 | ± | ± |
| pH 4 | + | + |
| pH 9 | + | + |
| pH 10 | + | ± |
| pH 11 | + | ± |
| pH 12 | ± | − |

+ = Stable
± = Stable under certain conditions
− = Unstable

We claim:

1. A compound of the formula

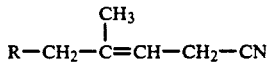

where R is a branched or straight-chain alkyl radical of 6 to 10 carbon atoms.

2. 4,7,9,9-Tetramethyldec-3-enenitrile.
3. 4-Methyltridec-3-enenitrile.
4. 4-Methyldodec-3-enenitrile.
5. A method of imparting fragrance properties to perfumes or to products to be perfumed, or for improving or modifying the fragrance properties of perfumes or of said products, comprising adding a compound as claimed in claims 1, 2, 3, or 4.